United States Patent [19]

Nocito et al.

[11] Patent Number: 4,922,030
[45] Date of Patent: May 1, 1990

[54] METHOD OF PREPARIG HALOGENATED NITROALCOHOLS

[75] Inventors: Vincent Nocito, Buffalo Grove; Louis J. Bedell, Mt. Prospect; Matthew I. Levinson, Chicago, all of Ill.

[73] Assignee: Angus Chemical Company, Northbrook, Ill.

[21] Appl. No.: 279,525

[22] Filed: Dec. 5, 1988

[51] Int. Cl.$^5$ .................. C07C 79/18; C07C 79/16
[52] U.S. Cl. .................................. 568/713; 568/712
[58] Field of Search .................. 568/713, 712, 709

[56] References Cited

U.S. PATENT DOCUMENTS

| | | | |
|---|---|---|---|
| 3,542,884 | 11/1970 | Adolp | 568/713 |
| 3,658,921 | 4/1972 | Wessendorf | 568/713 |
| 3,711,561 | 1/1973 | Wessendorf | 568/713 |
| 4,581,178 | 4/1986 | Milstein | 568/713 |

FOREIGN PATENT DOCUMENTS 161717 8/1964 U.S.S.R. .................. 568/713

Primary Examiner—Werren B. Lone
Attorney, Agent, or Firm—Leydig, Voit & Mayer

[57] ABSTRACT

A method of preparing bromonitroalcohols of the formula

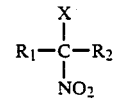

where $R_1$ is H, lower alkyl or $R_2$, $R_2$ is $R_3$CHOH in which $R_3$ is H, alkyl or aryl, and X is a halogen, which comprises reacting a halonitroalkane with a substantially nonaqueous solutioln of an aldehyde of the formula $R_3$CHO where $R_3$ is as noted above, in the presence of an alkaline catalyst. $R_3$ preferably is lower alkyl or monocyclic aryl such as phenyl.

12 Claims, No Drawings

METHOD OF PREPARING HALOGENATED NITROALCOHOLS

This invention is in the field of chemical synthesis and is directed to a method for the preparation of halonitroalcohols.

BACKGROUND OF THE INVENTION

The preparation of bromonitroalcohols is described in U.S. Pat. No. 3,658,921. The disclosed process comprises reacting a nitroalkane with an aldehyde and an inorganic salt of a member of the group consisting of magnesium and alkaline earth metals in an aqueous medium to form the magnesium or alkaline earth metal salt of a nitroalcohol. This nitroalcohol salt is then brominated without isolation in an aqueous suspension at a temperature below 25° C.

More recent U.S. Pat. No. 3,711,561 also describes a process for preparing bromonitroalcohols. The disclosed process comprises reacting a nitroalkane with an aldehyde and an alkali metal hydroxide in the presence of water to obtain an aqueous solution of the alkali metal salt of the nitroalcohol and reacting the aqueous solution with bromine at a temperature less than 25° C.

Both of these patents disclose that procedures involving the isolation of the salts of the nitroalcohols cause great difficulties. These difficulties include the very time consuming filtration and purification of such salts and the high instability of these salts. The patents disclose that attempts have been made to avoid these difficulties by effecting the halogenation step before the added condensation by first halogenating the nitroalkane to form the corresponding halonitroalkane and reacting the halonitroalkane with an aldehyde to form the halonitroalcohol. While this process is said to have been quite good in the case of long chain nitroalkanes, unsatisfactory results are said to have been obtained with short chain nitroalkanes, particularly with nitromethane.

BRIEF SUMMARY OF THE INVENTION

It is an object of the present invention to provide an improved method of preparing halonitroalcohols.

It is a further object of this invention to provide a method of preparing halonitroalcohols from short chain nitroalkanes while overcoming the problems described in the prior art.

Yet another object of this invention is to provide a method of preparing halonitroalcohols of high purity.

A still further object of this invention is to provide for a process for the preparation of halonitroalcohols which can be operated as either a batch or a semi-continuous process.

These and other objects and advantages of this invention, as well as additional inventive features, will become apparent from the description which follows.

Halonitroalcohols are prepared in accordance with the present invention by reacting a halonitroalkane with a substantially nonaqueous solution of an aldehyde in the presence of an alkaline catalyst and recovering the resultant halonitroalcohol.

DETAILED DESCRIPTION OF THE INVENTION

While the invention will be described in connection with certain preferred embodiments, it is not intended to limit the invention to the particular embodiments. On the contrary, it is intended to cover all alternatives, modifications, and equivalent processes as may be included within the spirit and scope of the invention as defined by the appended claims.

The present invention constitutes a method of preparing halogenated nitroalcohols of the formula:

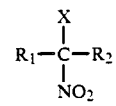

where $R_1$ is H, lower alkyl or $R_2$, $R_2$ is $R_3CHOH$ in which $R_3$ is H, alkyl or aryl, and X is a halogen. $R_3$ preferably is lower alkyl or monocyclic aryl such as phenyl. The inventive method involves the reaction of a halonitroalkane with a substantially nonaqueous solution of an aldehyde of the formula $R_3CHO$ where $R_3$ is as noted above, in the presence of an alkaline catalyst to form the halonitroalcohol which is subsequently recovered from the reaction mixture.

The halonitroalkane may be prepared by any procedure, such as the procedures disclosed in U.S. Pat. Nos. 2,309,806 and 3,096,378, although the following procedure, which is the subject of copending U.S. application Serial No. 279526 filed of even date herewith and whose disclosure is incorporated herein by reference, is preferred.

The preferred method involves the reaction of a nitronate salt, with a halogen to form the monohalogenated nitroalkane which is subsequently recovered from the reaction mixture.

The nitronate salt is prepared by reacting essentially equal molar quantities of an alkali metal hydroxide and a primary nitroalkane such as nitromethane, nitroethane, or 1-nitropropane. The reaction may take place in any suitable vessel equipped with an agitator and cooling jacket or may be performed in a continuous reactor consisting of a tube containing a static mixer. The reaction takes place at temperatures below about 40° C. and when in a batch operation at low temperature, e.g., 0° C.±10° C., and preferably in an aqueous medium in which an aqueous solution of the nitroalkane is mixed with an aqueous solution of the alkali metal hydroxide, resulting in an aqueous solution of the nitronate salt. Other solvents can also be used. The preferred alkali metal hydroxide is sodium hydroxide, but other alkali metal hydroxides can be utilized in the practice of the present invention.

The nitronate salt thus formed is promptly mixed with a halogen in equal molar quantities. Again, the reaction may take place in any suitable vessel. Preferably, an aqueous nitronate salt solution is charged into a reactor containing a solution of the halogen. Cooling is supplied to maintain the vessel at low temperature as recited in the preceding paragraph, with agitation. If a continuous system is desired, anhydrous halogen or a halogen solution can be fed into a tube reactor equipped with a static mixer simultaneously and in equal molar quantity with the nitronate salt solution. The process is preferably operated in an aqueous system, although other solvent systems can also be utilized. For example, if the halogen is not sufficiently water-soluble, a different, more suitable, solvent for the halogen may be used.

Immediately following formation of the monohalogenated nitroalkane, the solution is treated with a compound to destroy any unreacted halogen in the reaction mixture. The compound employed to destroy any unreacted halogen is preferably sodium bisulfite and is preferably added to the reaction mixture in the form of a saturated solution.

The resulting monohalogenated nitroalkane is recovered from the reaction mixture, preferably by distillation of a solvent azeotrope of the desired product and separation of the bottom product layer by decantation from a suitable distillation trap. The monohalogenated nitroalkane produced by this process will be on the order of 90–95% pure.

Preparation of the desired nitroalcohol is accomplished by reacting the halonitroalkane with a substantially nonaqueous aldehyde solution in the presence of an alkaline catalyst. While any suitable aldehyde may be used, formaldehyde is the commercially preferred aldehyde. Any suitable solvent or mixture of solvents may be used for the aldehyde, so long as the solvent is substantially nonaqueous. Methanol is the preferred solvent. Either inorganic or organic catalysts may be used. Suitable catalysts include sodium carbonate, sodium bicarbonate, sodium hydroxide, potassium hydroxide, triethyl amine, and n-butyl amine. Primary and secondary amines such as trishydroxymethyl amino methane and morpholine, however, do not function well as the catalyst. Sodium hydroxide is the preferred catalyst. The reaction is exothermic, and the temperature is controlled to maintain the reaction temperature between about 20°–60° C.

Following completion of the above reaction, the resulting halonitroalcohol can be recovered by any suitable means, preferably by lowering the temperature of the reaction material to about 25° C. in an agitated crystallizer with filtration of the crystals. Following filtration, additional crops of crystals can be obtained in this manner by further lowering the temperature and concentrating the mother liquor. The recovered halonitroalcohol has a purity on the order of 95–99%.

The following examples further illustrate the present invention but, of course, should not be construed as in any way limiting its scope.

EXAMPLE 1

This example illustrates the batch conversion of nitromethane to monobromonitromethane.

An aqueous nitromethane solution (10% wt. %) was prepared from nitromethane (500 g, 98.4%, 8.06 moles) and water (4,500 g). The aqueous nitromethane solution and an aqueous sodium hydroxide solution (1,638.3 g, 20% wt. %, 8.2 moles) were pumped into a four-neck, 500 ml, round-bottom flask equipped with a mechanical stirrer, thermometer, overflow tube, and immersed in a dry ice-acetone bath. The two streams were controlled with precision metering pumps and were contacted just prior to entering the vessel in a mixing T through which nitrogen was sparged to facilitate mixing and inert the flask. The rate of pumping was controlled so that nitromethane and caustic were reacted in a 1:1 molar ratio to form a nitronate salt and the net out fall from the overflow tube was 50.85 cc/min. The liquid level in the flask was controlled by raising or lowering the overflow tube so the vessel was half full. The pot temperature was maintained at −5° to 0° C. with cooling.

The nitronate salt solution overflow from this 500 ml flask was directed through a polypropylene tube subsurface into a four-neck, 12 liter, round-bottom flask equipped with a mechanical stirrer, thermometer, and dry ice vapor trap and which was charged with water (1,000 g) and bromine (8.2 moles, 1,310.6 g). The pot temperature in the 12 liter vessel was maintained at −5 to 0° C. by immersion in a dry ice-acetone bath.

Following completion of the nitronate salt solution addition to the bromine solution, the dark red monobromonitromethane solution was stirred for 15 minutes. A charge of saturated sodium bisulfite solution (25 cc) was then added to destroy the unreacted bromine, whereupon the reaction mixture turned colorless.

Agitation was then stopped and the entire reactor contents were transferred to a 12 liter round-bottom flask equipped with a mechanical stirrer, thermometer, and a Vigreux distillation column topped with a Dean-Stark trap and a cold water condenser.

An impure azeotropic forecut was taken (head temperature was 90°–94° C.) and the main product cut was collected as a 1:1 water azeotrope (head temperature=94°–101° C., pot temperature=100°–105° C., 760 mm Hg). The colorless lower monobromonitromethane layer was drawn off semicontinuously during the course of distillation and the upper aqueous layer was allowed to overflow back to the pot.

The product thus collected (1,088.3 g) was assayed by GLPC internal standard analysis as consisting of 90.5 wt. % monobromonitromethane, approximately 1.4 wt. % bromonitroethane, and approximately 2.4 wt. % dibromonitromethane. The conversion of nitromethane (500 g, 98.4%, 8.06 moles) to monobromonitromethane (985 g, 7.03 moles) was 87.28 mole percent.

EXAMPLE 2

This example illustrates the preparation of 2-bromo-2-nitro-1,3-propanediol ("bronopol") using the bromonitromethane prepared in Example 1.

To a four-neck, two liter, round-bottom flask, equipped with a mechanical stirrer, thermometer, pH probe, dropping funnel, and caustic inlet feed tube was charged a 55 wt. % formaldehyde in methanol solution (731 g, 13.4 moles). The dropping funnel was charged with the bromonitromethane from Example 1 (900 g, 90.5 wt. %, 5.80 moles). Stirring was commenced and 50% caustic was added dropwise until a pH of 9.0–10.0 was achieved. The bromonitromethane was then introduced dropwise at such a rate that the total charge would be added in two hours. The reaction temperature was allowed to climb to 45° C. and was maintained at this point by immersion of the flask in an ice water bath.

The pH of the reaction mixture was allowed to decrease to 8.3 and was then maintained in the range of pH 8.3–8.7 by dropwise addition of 50% caustic (total charge approximately 5 g, 0.063 moles). Following completion of the bromonitromethane addition, the cooling bath was removed immediately and the pH was raised to 8.8. The reaction mixture was stirred for 15 minutes at 40°–45° C. Following a holding period the pH was adjusted to 3.5–5.5 with concentrated Hcl and a seed crystal was introduced. The reaction mixture was then cooled slowly to 25° C. over a two to four hour period with continued stirring.

The crystalline product was collected by suction filtration of the methanolic slurry through a coarse sintered filter and air-dried for 24 hours giving 99 wt. % purity bronopol (696 g, 3.45 moles). This was a yield of 59.4 mole percent from the bromonitromethane.

The mother liquor was then recharged to the crystallizing vessel and cooled slowly to 5° C. before collecting a second crop of crystalline product of 99 wt. % bronopol (198 g, 0.98 moles), giving an additional 16.8 mole percent conversion from bromonitromethane, for a total recovery of 76.2 mole percent based on the bromonitromethane. The mother liquor collected off the second crop (637 g) assayed at 40.1 wt. % bronopol (255.4 AI, 1.28 moles) accounting for 22.05 mole percent of the reactant charge for an overall molar balance of 98.33%.

EXAMPLE 3

This example sets forth a procedure for the preparation of monochloro-nitromethane.

The apparatus used to prepare monochloronitromethane included three reactors: a nitronate reactor, a chlorination reactor, and a distillation reactor. The nitronate reactor was a 500 ml, round-bottom flask equipped with a thermometer, agitator, two feed reservoirs and pumps, and a nitrogen purge line. The chlorination reactor was a 12 liter, round-bottom flask equipped with a dry ice reflux condenser, inlets for chlorine and nitronate, an agitator, and a scrubber (10% NaOH/10% NaHSO$_3$). The distillation reactor was a 12 liter, round-bottom flask equipped with a thermometer, agitator, 1.5 feet Vigreux column, a Dean-Stark trap, and a scrubber (10% NaOH/10% NaHSO$_3$).

The following procedure was followed in preparing the monochloronitromethane. 6,100 grams of a 10 percent aqueous nitromethane (10 moles) solution was charged to the feed tank of the nitronate reactor, and 2,000 grams of a 20 percent sodium hydroxide (10 moles) solution was charged to the second feed tank of the nitronate reactor. The overflow nitronate reactor (500 ml) was charged with 150 ml of DI water and then cooled to 0° C. with a dry ice-acetone bath. The dip pipe of the nitronate reactor was adjusted to give a residence time of three minutes at a feed rate of 53.3 cc per minute.

The chlorination reactor was charged with one liter of methylene chloride and then cooled to −5° C. with a dry ice-acetone bath. The agitator was then started. Chlorine was sparged into the methylene chloride until a gentle reflux of liquid chlorine was apparent in the dry ice reflux condenser. At that time, the flow of nitrogen was started to the nitronate reactor (20 cc/minute). After two minutes, the nitromethane feed pump was started (41.5 ml/minute) along with the sodium hydroxide feed pump (11.8 ml/minute). The temperature in the nitronate reactor was continuously monitored and maintained at 0°-5° C.

The flow of chlorine to the chlorination reactor was then continued (feed rate: 8.5 grams/minute for the first 40 minutes, 5.95 grams/minute for the next 30 minutes, 2.55 grams/minute for the final 55 minutes). The sodium nitronate solution (yellow) overflowed continuously to the chlorination reactor, and the temperature in the chlorination reactor was maintained at 0°-5° C. A total of 760 grams of chlorine was fed to the reactor (10.7 moles) over the 2.6 hour nitronate feed period.

Upon completion of the feed addition, the nitronate pumps were stopped. The reaction mixture was allowed to warm to 25° C. and then stirred for one hour. The solution was cloudy yellow with a bright yellow organic phase at the bottom.

The entire contents of the reaction flask were transferred to the distillation reactor. The reaction mixture was heated to boiling (atmospheric pressure), and the scrubber was used to remove chlorine evolved during the heating. A forecut was collected up to a head temperature of 91° C. The product cut was collected as the bottom layer of the azeotrope between 91°-101° C. (head; 94°-104° C. pot).

By following the foregoing procedure, 824 grams of product was recovered containing 88 wt. % monochloronitromethane, 2-3 wt. % dichloronitromethane, 1-2 wt. % trichloronitromethane, and 5-7 wt. % nitromethane. It is believed that the nitromethane in the product could have been removed from the recovered product by increasing the temperature of the forecut to 94° C.

EXAMPLE 4

This example illustrates the preparation of 2-chloro-2-nitro-1,3-propanediol ("chloropol") using chloronitromethane prepared in a manner similar to that used to prepare the chloronitromethane of Example 3.

1,816-grams of methyl formcel (55 percent CH$_2$O, 35 percent MeOH, 10 percent H$_2$O, 33.26 moles CH$_2$O) were charged into a four liter resin kettle, equipped with a thermometer, pH probe and controller, agitator, chloronitromethane feed pump, and NaOH feed pump. The reactor was cooled to 15° C. in an ice water bath, and the agitator was started.

The pH controller was started, and the reaction mixture was adjusted to an initial pH of 10 by metered addition of 50 percent NaOH.

1,543.2 grams of 88 wt. % chloronitromethane prepared in a manner similar to that set forth in Example 3 was charged to the feed tank. The pH controller was set to 8.5, and the chloronitromethane feed pump (25.7 grams/minute) was started. The temperature was allowed to rise to 55° C., with cooling being applied as needed. Care was taken not to allow the pH to drop below 8.5 by use of NaOH charges of about 17 grams. The chloropol began to crystallize toward the end of the chloronitromethane addition.

The reaction mixture was stirred for 45 minutes at 55° C. upon completion of the chloronitromethane addition. The chloropol solution was then cooled to 35° C., and the pH was quenched to 5.4 with concentrated HCl.

Cooling was continued until the chloropol slurry reached 25° C., whereupon a first crop of chloropol (1,562.8 grams) was collected. The mother liquor was then cooled and concentrated, and a second crop (444.8 grams) and third crop (114.0 grams) of crystals at 10° C. and 0° C., respectively, were collected. Total yield of chloropol was 2,121.6 grams (13.6 moles, 92 percent molar yield) with an average purity of 96 percent.

EXAMPLES 5-10

These examples illustrate the preparation of bronopol using various catalysts and reaction conditions.

In each of the examples, a solution of 40.0 g (0.29 mole) of monobromonitromethane and 70 ml of methanol was added to 31.2 g (0.57 mole) of a 55% formaldehyde solution in methanol at 20° C. The addition was completed in 12 minutes and the maximum reacting temperature during addition was 27° C. 0.014 mole of an alkaline catalyst was included in the formaldehyde solution. The reaction mixture was held for various lengths of time and temperature. The specific catalysts and reaction conditions, along with the bronopol yields, are set forth in the table below.

| Example | Catalyst | Wt. of Catalyst | Yield of Bronopol | Reaction Time | Reaction Temp. |
|---|---|---|---|---|---|
| 5 | sodium bicarbonate | 1.2 g | 36 g | 21 hours | 27–33° C. |
| 6 | sodium hydroxide | 0.57 g | 40.6 g | 2.5 hours | 20–23° C. |
| 7 | potassium hydroxide | 0.80 g | 41.5 g | 3 hours | 22–26° C. |
| 8 | sodium carbonate | 1.52 g | 39.5 g | 3.5 hours | 23–27° C. |
| 9 | triethyl amine | 1.45 g | 51.6 g | 3.5 hours | 23–26° C. |
| 10 | n-butyl amine | 1.05 g | 11.6 g | 22 hours | 23–28° C. |

EXAMPLES 11-14

These examples illustrate the preparation of bronopol using various amounts of catalysts.

In each of the examples, a solution of 40.0 g (0.29 mole) monobromonitromethane and 70 ml of methanol was added in 18 minutes to a 55% formaldehyde solution in methanol maintained at 18° C. and containing various levels of alkaline catalyst. The reaction temperature was allowed to rise to 30° C. during the addition. Following the addition, the solution was heated to 60° C. and held there for three hours. The solution was then cooled to 20° C. and the pH adjusted to 4.3 with 1.0 molar aqueous HCl. The specific catalysts and amounts used thereof, as well as the resulting yields of bronopol, are set forth in the table below.

| Example | Catalyst | Wt. of Catalyst | Yield of Bronopol |
|---|---|---|---|
| 11 | sodium bicarbonate | 1.20 g | 51.7 g |
| 12 | sodium bicarbonate | 0.72 g | 24.6 g |
| 13 | sodium bicarbonate | 1.68 g | 50.3 g |
| 14 | sodium hydroxide | 1.6 g | 48 g |

EXAMPLES 15-19

These examples illustrate the preparation of halonitroalcohols using various aldehydes. In these examples the halonitroalcohols were prepared utilizing the following general procedure.

Aldehyde was blended with methanol in a flask and the pH of the resulting solution is adjusted with a 30% NaOH solution to between 9.5 and 12. This as well as the reaction of aldehyde and halonitroalcohol is exothermic. A cooling medium such as a water bath was utilized to prevent the temperature from becoming greater than 50° C. The halonitroalkane is added dropwise to the alkaline aldehyde solution and the pH is monitored and adjusted as necessary to maintain the pH between 8-9.5. After addition of the halonitroalkane the solution was held with agitation for an additional 30 minutes. pH was then adjusted to 2-4 with HCl. The resulting halonitroalcohol was recovered by concentration at 40° C., 10 mm Hg.

The following aldehydes and halonitroalkanes were used to produce the product indicated.

| Example | Aldehyde | Halonitroalkane | Halonitroalcohol |
|---|---|---|---|
| 15 | isobutaldehyde | chloronitromethane | 4-chloro-2,6-dimethyl-4-nitro-3,5-heptanediol |
| 16 | octyladehyde | bromonitromethane | 9-bromo-9-nitro-8,10-heptadecanediol |
| 17 | propionaldehdye | bromonitromethane | 4-bromo-4-nitro-3,5-heptanediol |
| 18 | benzaldehyde | bromonitromethane | 2-bromo-1,3-diphenyl-2-nitro-1,3-propanediol |
| 19 | benzaldehyde | chloronitromethane | 2-chloro-1,3-diphenyl-2-nitro-1,3-propanediol |

What is claimed is:

1. A method of preparing a halonitroalcohol of the formula

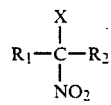

where $R_1$ is H, lower alkyl or $R_2$, $R_2$ is $R_3$CHOH in which $R_3$ is H, lower alkyl or phenyl, and X is chloro or bromo, which comprises reacting at a temperature between about 20° C. and 60° C. a halonitroalkane with a substantially nonaqueous solution of an aldehyde of the formula $R_3$CHO where $R_3$ is as noted above, in the presence of an alkaline catalyst and recovering the resultant halonitroalcohol.

2. The method of claim 1 wherein $R_1$ is hydrogen or lower alkyl.

3. The method of claim 1 wherein $R_1$ is $R_2$.

4. The method of claim 3 wherein the aldehyde is formaldehyde.

5. The method of claim 4 wherein the alkaline catalyst is selected from the group consisting of sodium carbonate, sodium bicarbonate, sodium hydroxide, potassium hydroxide, triethyl amine, and n-butyl amine.

6. The method of claim 5 wherein the solvent for the formaldehyde is substantially methanol.

7. The method of claim 6 wherein the halonitroalkane is halonitromethane and the halonitroalcohol is halonitropropanediol.

8. The method of claim 7 wherein the halogen is chlorine or bromine.

9. The method of claim 8 wherein the halonitroalkane is bromonitromethane and the halonitroalcohol is 2-bromo-2-nitro-1,3-propanediol.

10. The method of claim 9 wherein the halonitroalkane is chloronitromethane and the halonitroalcohol is 2-chloro-2-nitro-1,3-propanediol.

11. The method of claim 1 wherein the halonitroalcohol is prepared in a semi-continuous process.

12. The method of claim 1 wherein the halonitroalcohol is prepared in a batch process.

* * * * *